United States Patent [19]
Keisz

[11] Patent Number: 5,971,974
[45] Date of Patent: *Oct. 26, 1999

[54] LEFT CORONARY ARTERY CATHETER

[75] Inventor: Radoslaw Stefan Keisz, San Antonio, Tex.

[73] Assignee: Schneider ( USA ) Inc, Plymouth, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/707,458
[22] Filed: Sep. 3, 1996

Related U.S. Application Data

[60] Provisional application No. 60/003,309, Sep. 6, 1995.
[51] Int. Cl.$^6$ .................................................. A61M 25/00
[52] U.S. Cl. ............................................. 604/523; 604/264
[58] Field of Search .............................. 604/280, 53, 93, 604/171, 264, 270, 281, 523; 128/658

[56] References Cited

U.S. PATENT DOCUMENTS

| | | | |
|---|---|---|---|
| 4,735,620 | 4/1988 | Ruiz | 604/281 |
| 4,883,058 | 11/1989 | Ruiz | 128/654 |
| 4,973,306 | 11/1990 | Ruiz | 604/53 |
| 5,016,640 | 5/1991 | Ruiz | 128/658 |
| 5,188,619 | 2/1993 | Myers | 604/280 |
| 5,203,776 | 4/1993 | Durfee | 604/264 |
| 5,299,574 | 4/1994 | Bower | 128/658 |
| 5,322,509 | 6/1994 | Rickerd | 604/53 |
| 5,401,258 | 3/1995 | Voda | 604/281 |
| 5,445,624 | 8/1995 | Jimenez | 604/280 |
| 5,470,322 | 11/1995 | Horzewski et al. | 604/280 |
| 5,497,774 | 3/1996 | Swartz et al. | 128/658 |
| 5,527,274 | 6/1996 | Zakko | 604/28 |
| 5,531,721 | 7/1996 | Pepin et al. | 604/282 |
| 5,569,218 | 10/1996 | Berg | 604/282 |
| 5,584,803 | 12/1996 | Stemens et al. | 604/4 |
| 5,584,821 | 12/1996 | Hobbs et al. | 604/280 |
| 5,814,029 | 9/1998 | Hassett | 604/281 |
| 5,868,700 | 2/1999 | Voda | 604/49 |

FOREIGN PATENT DOCUMENTS

| | | | |
|---|---|---|---|
| 0 728 494 A1 | 8/1996 | European Pat. Off. | A61M 25/00 |
| 92 15 779 | 3/1993 | Germany | A61M 25/00 |
| WO 92/12754 | 8/1992 | WIPO | A61M 25/00 |
| WO 93/14802 | 8/1993 | WIPO | A61M 25/00 |
| WO 93/21983 | 11/1993 | WIPO | A61M 25/00 |
| WO 95/15780 | 6/1995 | WIPO | A61M 25/00 |

OTHER PUBLICATIONS

Mallinckrodt Diagnostic Catheters, 1990, Mallinckrodt Medical Inc.

Meditech Angiographic Catheters, Boston Scientific Coporation.

International Search Report, PCT/US96/14224, mailed Dec. 12, 1996, (3 pages).

Diagnostic Catheters: from Mallinckrodt and Medi–tech (5 pages), Oct. 1990.

U.S. Ser. No. 08/560251, Catheter For Percutaneous Transradial Approach, filed Nov. 21, 1995.

Illustrations of Amplatz AL3 7F, AL2 8F and XLT 3.5 8F catheters (2 pages).

Primary Examiner—Corrine McDermott
Assistant Examiner—Cris L. Rodriguez
Attorney, Agent, or Firm—Faegre & Benson LLP

[57] ABSTRACT

A left coronary catheter including a hub, a linear flexible tubular body stock extending from the hub and a curved flexible tubular stem extending from the body stock. The curved stem includes a first, arcuate section extending from a distal end of the body stock, a second, arcuate section from a distal end of the first section, a third, arcuate section extending from a distal end of the second section, and a fourth, linear section including a soft tip extending from a distal end of the third section. The first and second sections curve toward the body stock. The third section curves away from the body stock.

41 Claims, 4 Drawing Sheets

LEFT CORONARY ARTERY CATHETER

REFERENCE TO RELATED APPLICATION

This application claims the benefit of U.S. Provisional Application No. 60/003,309, filed on Sep. 6, 1995.

BACKGROUND OF THE INVENTION

1. Field of the Invention

The present invention relates generally to coronary catheters. In particular, the present invention is a catheter for use in connection with medical procedures on the left coronary artery.

2. Description of the Related Art

Catheters used in connection with medical procedures on the coronary system are generally known and disclosed, for example, in the following U.S. patents, all of which are hereby incorporated by reference in their entirety and for all purposes:

| Inventor | U.S. Pat. No. |
| --- | --- |
| Ruiz | 4,973,306 |
| Ruiz | 4,735,620 |
| Bower | 5,299,574 |
| Rickerd | 5,322,509 |
| Voda | 5,401,258 |

Coronary catheters of the type described in the above-identified patents typically include an elongated and flexible tubular member mounted to a hub. The tubular member includes a relatively long and generally straight section sometimes referred to as the body stock which extends from the hub, and a nonlinear or curved section sometimes referred to as the stem which extends from the body stock. The distal end of the stem is often terminated with a tip.

The size, flexibility and other characteristics of catheters will vary depending upon their intended use. One particular type of catheter used for catheterization of the left coronary artery is known as a left coronary catheter. Left coronary catheters are inserted tip first into the femoral, brachial or radial artery of the patient and directed upwardly through the aorta until the tip is positioned adjacent to and engaged with the ostium or opening of the left coronary artery. During this catheterization procedure the tip of the catheter passes in sequence through the descending aorta, the aortic arch and the ascending aorta. Once it has been inserted, the catheter can be used for a wide variety of medical procedures. By way of example, interventional devices such as stents, rotational and directional atherectomy devices, guidewires and other devices can be deployed to the left coronary artery through the lumen in the catheter. Catheters of this type can also be used to guide and support balloon dilation catheters for percutaneous transluminal coronary angioplasty (PTCA) or percutaneous transluminal peripheral angioplasty (PTA), and for injecting dyes and other contrast media into the artery in connection with these procedures.

To be efficacious, left coronary catheters must be capable of being quickly inserted and removed from the aorta. The catheters must also be capable of accurately positioning their tips at the ostium of the artery being treated, without suddenly extending into and damaging the artery, a characteristic known as diving. The catheter also must provide a back-up support since after it is inserted, a force known as the deployment force will be exerted on the interventional device being directed to the artery through the catheter. Without sufficient back-up support insertion of an interventional device may not be possible and trauma to the body vessels or ostium may occur. It is desirable that the inserted catheter be capable of retaining its position to allow the interventional device to be accurately deployed within the artery, even if relatively high deployment force is required. The catheter should, of course, be capable of providing these characteristics and properties while avoiding damage to the body vessels through which it is directed.

The shape of the catheter stem is an important factor contributing to the overall success of the procedures described above. Decisions on whether a given device can be delivered to a treatment site and the procedure successfully performed often depend upon the ability to appropriately catheterize the patient. There is, therefore, a continuing need for catheters having improved stem shapes.

SUMMARY OF THE INVENTION

The present invention is a left coronary catheter which can be efficiently inserted to and removed from the ostium of a patient's left coronary artery through the descending aorta, aortic arch and ascending aorta. The catheter can also be positioned in the ostium of the left coronary artery with a relatively high degree of accuracy. One embodiment of the catheter comprises a flexible and tubular body stock and a flexible and tubular stem extending from a distal end of the body stock. The stem may include a tip on its distal end, a first arcuate section between the tip and body stock, a second arcuate section between the first section and the tip, and a third arcuate section between the second section and the tip. The first, second and third arcuate sections each have an associated free state radius and free state arc length. The first free state radius of the first section is greater than the second free state radius of the second section, and the first free state arc length of the first section is greater than the second arc length of the second section. A portion of the stem including the first and second sections extends toward the body stock in its free state, while the third section extends away from the body stock in its free state. The radii and arc lengths of the first, second and third sections are adapted to cause the stem to engage a substantially continuous length of the contralateral wall of the ascending aorta from a location opposing the ostium of the left coronary artery when the catheter is positioned within the patient with the tip engaged with the ostium of the left coronary artery. The catheter therefore supports a relatively high deployment force.

In one preferred embodiment, the first, second and third sections of the stem are contiguous with each other and the body stock. The first section can have a free state arc length of 155° and a free state radius of 1 inch. The second section can have a free state arc length of 110° and a free state radius of 0.65 inches. The third section can have an arc length of 10°, 20° or 30° and a free state radius of 0.40 inches.

In yet another embodiment the stem includes a fourth linear section extending from the third section. The fourth section can have the length of 0.15 inches. The distal end is located on the end of the fourth linear section and is softer than the fourth section.

DETAILED DESCRIPTION OF THE PREFERRED EMBODIMENTS

Figure 1:
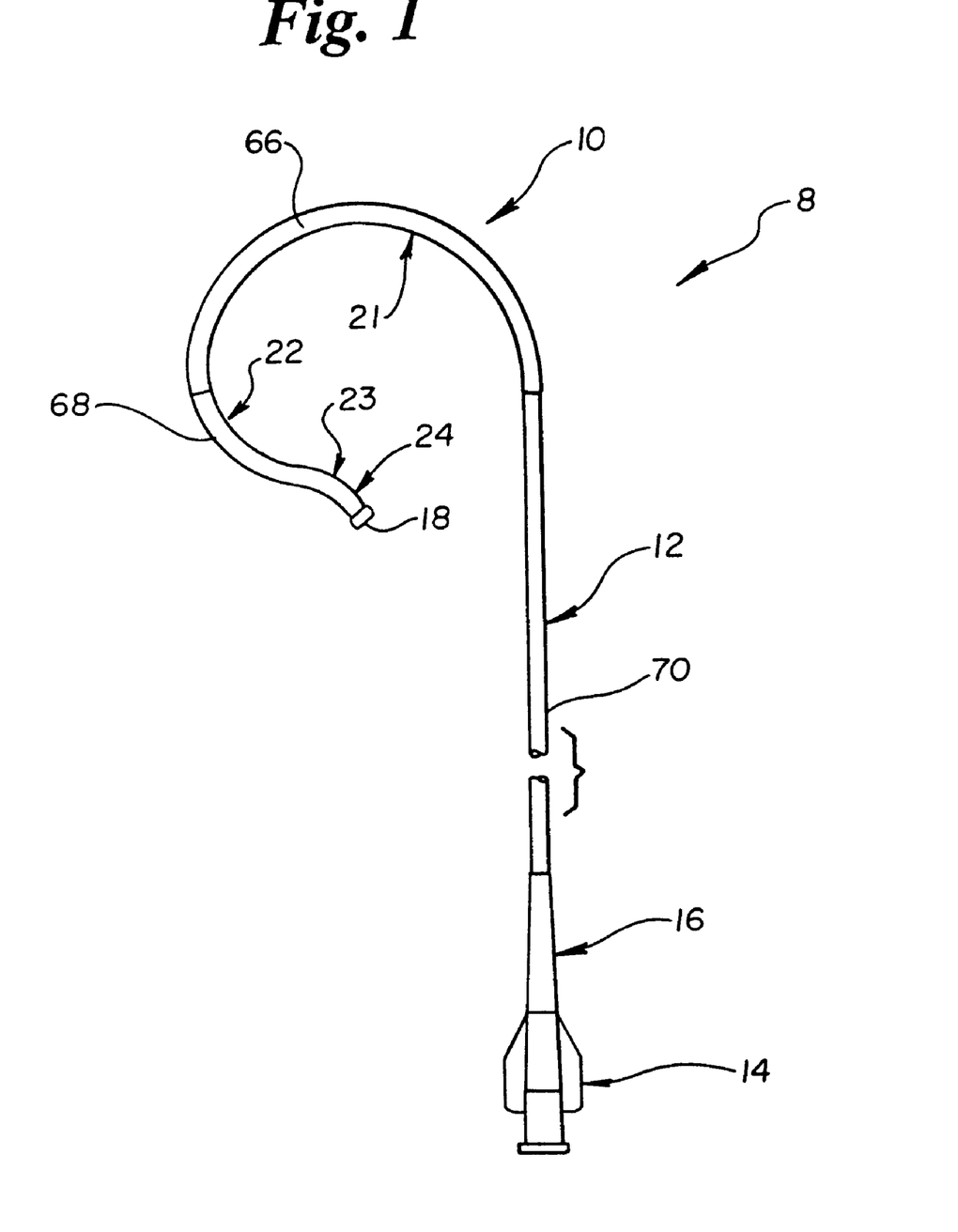
FIG. 1 is an illustration of a left coronary catheter having a nonlinear stem in accordance with the present invention.

A femoral, brachial or radial approach left coronary artery catheter 8 which includes a flexible tubular stem 10 in accordance with the present invention is illustrated generally in FIG. 1. As shown, stem 10 extends from the distal end of an elongated flexible tubular body stock 12. A hub 14 is attached-to a proximal end of body stock 8 by means of a strain relief 16. A relatively soft tip 18 is positioned on the distal end of stem 10 in the embodiment shown. As described in greater detail below, the shape of stem 10 enables the catheter 8 to be efficiently inserted and its distal end (e.g., tip 18) accurately and coaxially positioned in the ostium of the left coronary artery. Once positioned, the stem 10 extends along and engages a substantially continuous length of the contralateral wall of the ascending aorta to provide superior back-up support during the deployment of interventional devices.

The shape of stem 10 can be described in greater detail with reference to FIG. 2 where the stem is shown in its free state with no internal or external forces applied thereto. As shown, stem 10 includes a first arcuate section 21, a second arcuate section 22, a third arcuate section 23, a fourth linear section 24 and tip 18. First section 21 is positioned between the generally linear body stock 12 and tip 18 (i.e., is positioned between the body stock and distal end of stem 10, and is distally disposed from the body stock), and has a first free state arc length Al and a first free state radius RI. In the embodiment shown, first section 21 extends from and is contiguous with body stock 12, having a proximal end connected directly to the distal end of the body stock. Second section 22 is positioned between first section 21 and tip 18 (i.e., is distally disposed from the first section), and has a second free state arc length $A_2$ and a second free state radius $R_2$. In the embodiment shown, second section 22 extends from and is contiguous with first section 21, having a proximal end connected directly to the distal end of the first section. Third section 23 extends between second section 22 and tip 18 (i.e., is distally disposed from the second section), and has a third free state arc length $A_3$ and a third free state radius $R_3$. In the embodiment shown, third section 23 is contiguous with and extends from section 22, having a proximal end connected directly to the distal end of the second section. The fourth linear section 24, which includes tip 18, is contiguous with, disposed distally from, and extends from third section 23, having a proximal end which is connected directly to the distal end of the third section. Fourth section 24 has a length $L_4$ which includes the length of tip 18 in the convention used throughout this document.

Figure 2:
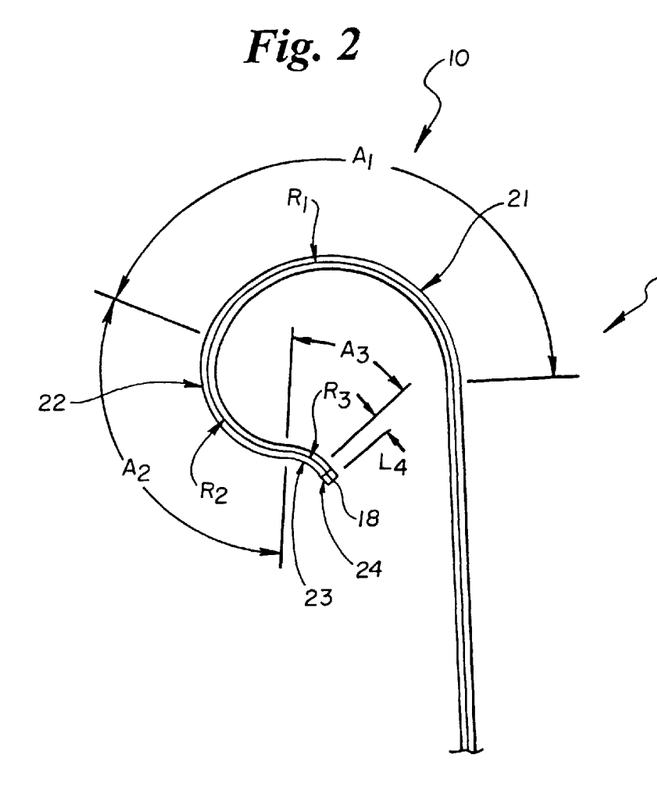
FIG. 2 is a detailed illustration of the stem of the catheter shown in FIG. 1.
Figure 3:
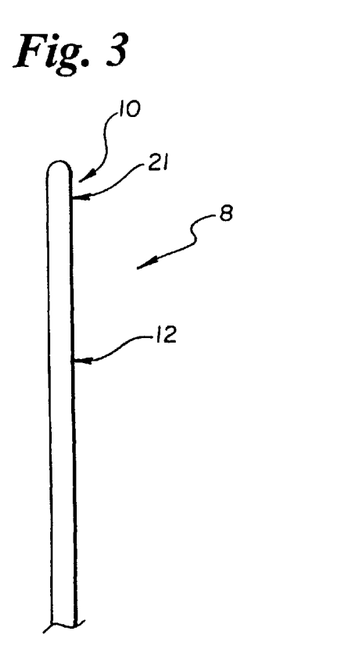
FIG. 3 is a side view of the catheter shown in FIG. 2, taken from the right side of FIG. 2.

FIG. 3 is a side view of the body stock 12 and stem 10, and is taken from the side. of the body stock opposite that of tip 18 (i.e., from the right side of the body stock as illustrated in FIG. 2). As is evident from FIG. 3, first through fourth sections 21–24 are oriented in the same plane in the illustrated embodiment of catheter 8. In other embodiments (not shown) sections 21–24 can extend (typically to a relatively limited extent) out of the planar configuration shown in FIGS. 2 and 3. Section 22 can be described as having a radius $R_2$ which is in the same direction as the radius $R_1$ of section 21, with the second section extending from the first section back toward body stock 12 in the direction of an inwardly closing loop. Third section 23 has a radius $R_3$ which is effectively in the opposite direction of radii $R_1$ and $R_2$, and extends away from body stock 12 in the direction of an outwardly closing loop.

Arc lengths $A_1$–$A_3$, radii $R_1$–$R_3$ and length $L_4$ can vary on the basis of a number of factors including the size of the coronary system of a patient with which the catheter 8 is intended to be used. It is anticipated that an efficacious range of first arc lengths $A_1$ is between about 120° and 180°, with a particularly efficacious range being between about 145° and 165°. An expected efficacious range of first radii $R_1$ is between about 0.5 and 1.5 inches, with a particularly efficacious range being between about 0.75 and 1.25 inches. An efficacious range of second arc lengths $A_2$ is between about 80° and 140°, with a range between about 100° and 120° being particularly efficacious. An expected efficacious range of second radii $R_2$ is between about 0.25 and 1.00 inches, with a particularly efficacious range being between about 0.40 and 0.80 inches. An expected efficacious range of third arc lengths $A_3$ is between about 5° and 45°, with arc lengths between about 10° and 30° being particularly advantageous. Third radii $R_3$ in the range between about 0.25 and 0.75 inches are anticipated as being efficacious, with radii between about 0.35 and 0.60 inches being particularly advantageous. An anticipated efficacious length $L_4$, including the length of tip 18, is in the range between about 0.10 and 0.75 inches, with lengths between about 0.10 and 0.25 inches being particularly efficacious. The length of tip 18 can range between about 0.10 and 0.40 inches.

Arc lengths $A_1$–$A_3$, lengths $L_4$ and radii $R_1$–$R_3$ for seven specific embodiments of catheter 8 including a stem 10 in accordance with the present invention are described below in Table 1 as Examples 1–7. The length of the body stock 12 of the catheter 8 represented by Examples 1–7 is in the range of about 34 to 38 inches. The tip 18 for each of these catheters 8 is 0.09 inches in length.

TABLE 1

| EXAMPLE NO. | $A_1$ (degrees) | $R_1$ (inches) (cm) | $A_2$ (degrees) | $R_2$ (inches) (cm) | $A_3$ (degrees) | $R_3$ (inches) (cm) | $L_4$ (inches) (cm) |
|---|---|---|---|---|---|---|---|
| 1 | 155 | 1.00 / 2.54 | 110 | 0.65 / 1.65 | 30 | 0.40 / 1.02 | 0.15 / 0.38 |

TABLE 1-continued

| EXAMPLE NO. | $A_1$ (degrees) | $R_1$ (inches) (cm) | $A_2$ (degrees) | $R_2$ (inches) (cm) | $A_3$ (degrees) | $R_3$ (inches) (cm) | $L_4$ (inches) (cm) |
|---|---|---|---|---|---|---|---|
| 2 | 155 | 1.00 / 2.54 | 110 | 0.65 / 1.65 | 20 | 0.40 / 1.02 | 0.15 / 0.38 |
| 3 | 155 | 1.00 / 2.54 | 110 | 0.65 / 1.65 | 10 | 0.40 / 1.02 | 0.15 / 0.38 |
| 4 | 155 | 1.00 / 2.54 | 110 | 0.75 / 1.91 | 20 | 0.40 / 1.02 | 0.15 / 0.38 |
| 5 | 155 | 1.00 / 2.54 | 110 | 0.75 / 1.91 | 10 | 0.40 / 1.02 | 0.15 / 0.38 |
| 6 | 155 | 0.85 / 2.16 | 110 | 0.40 / 1.02 | 20 | 0.55 / 1.40 | 0.15 / 0.38 |
| 7 | 155 | 1.00 / 2.54 | 110 | 0.55 / 1.40 | 20 | 0.40 / 1.02 | 0.15 / 0.38 |

In general, the catheter 8 described by Example 6 which has a second radius $R_2$ of about 0.04 inches (1.02 cm) is intended for patients having a relatively small aorta. Catheter 8 described by Examples 4 and 5 which have a radius $R_2$ of 0.75 inches (1.91 cm) is intended for patients having a relatively large aorta. Catheters described by Examples 1, 2, 3 and 5 will be used on patients having medium-sized aortas.

The catheters 8 of Examples 3 and 5 which have third arc lengths $A_3$ of about 10° will typically be used on patients having a superior or generally upwardly oriented take-off from the ostia into their left coronary artery. The catheters 8 of Examples 2, 4, 6 and 7 which have third arc lengths $A_3$ of about 20° will typically be used with patients having a normal or horizontal take-off of the left coronary artery. The catheter 8 of Example 1 which has a third arc length $A_3$ of about 30° can be used with patients having an inferior or generally descending take-off of their left coronary. By properly selecting a catheter 8 which matches the anatomic characteristics of the patient's left coronary artery take-off, the fourth linear section 24 can be generally coaxially aligned with the take-off when the catheter is positioned. Other combinations of radii $R_1$–$R_3$, arc lengths $A_1$–$A_3$ and lengths $L_4$ can provide the desirable insertion, removal, positioning and back-up support characteristics of stem 10 described herein.

A patient's anatomy can also be determined by radiographic analysis or other means. Based upon such an anatomy analysis, particular characteristics $R_1$–$R_3$, $A_1$–$A_3$ and $L_4$ can be selected and optimized for the particular patient.

Figure 4:
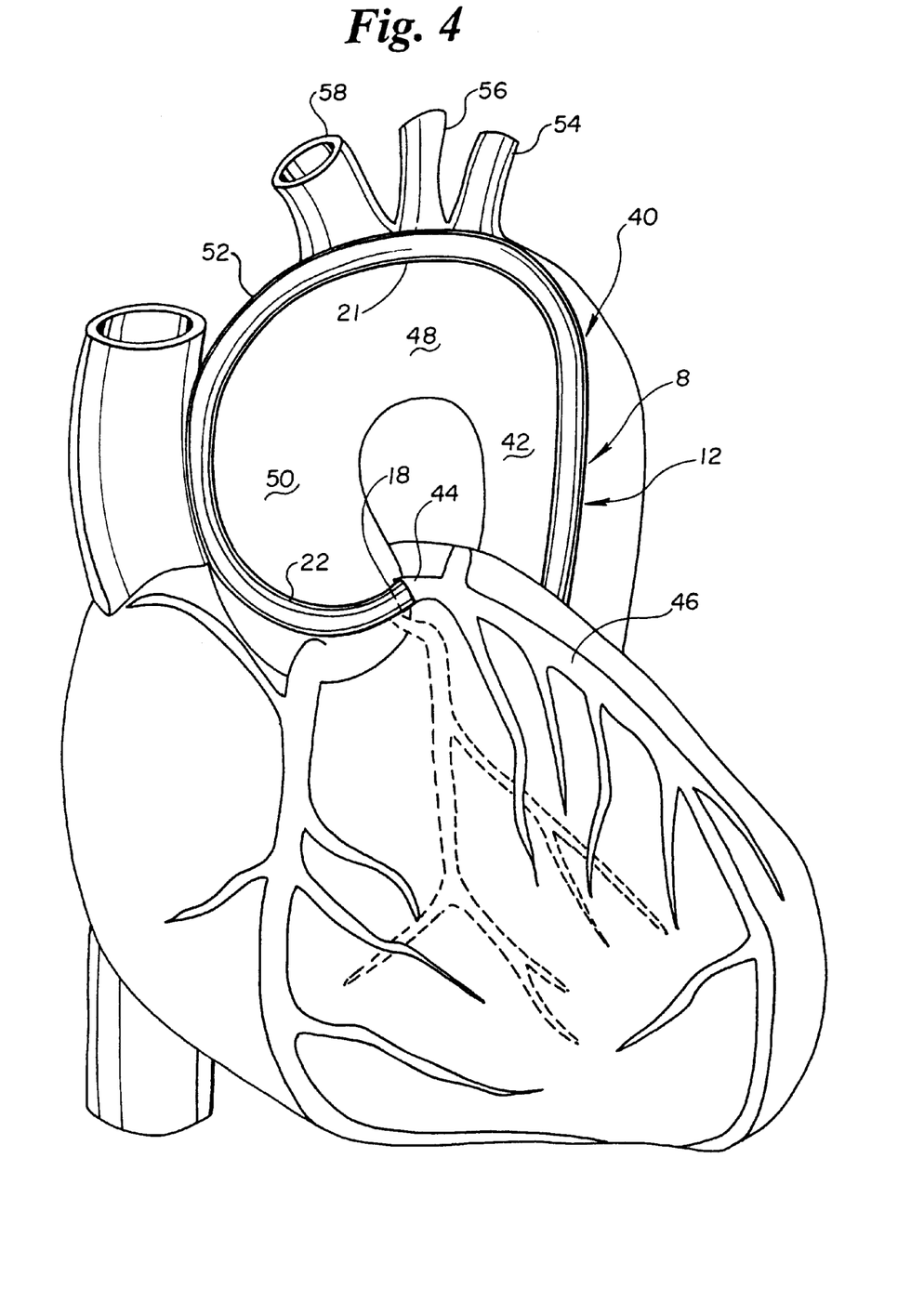
FIG. 4 is an illustration of a human heart with the catheter shown in FIG. 1 positioned therein with its tip adjacent to the ostium of the left coronary artery.

FIG. 4 illustrates the shape and position of catheter 8 after it has been inserted into an aorta 40 of a patient. As shown, the stem 10 of catheter 8 enters aorta 40 through the descending aorta 42 and engages ostium 44 of the left coronary artery 46 (e.g, at least the distal end of the catheter is within the ostium) after passing through the aortic arch 48 and into the ascending aorta 50. During catheterization procedures the distal end is often extended about 5 mm into the ostium. As shown, a length of stem 10 (i.e., an engagement portion) including a portion of the first arcuate section 21, and in most cases also a portion of the second arcuate section 22, is engaged with a continuous length (often preferably at least about 30–50 mm) of the contralateral wall 52 of the aorta 40, beginning at a location opposing the ostium 44 (i.e., at the same level as the ostium), and extending along the ascending aorta 40 toward the aortic arch 48. The first section 21 is engaged with contralateral wall 52 adjacent to the left subclavian artery 54, left common carotid artery 56 and brachiocephalic trnk 58 in the embodiment shown. The fourth linear section 24 is also coaxially engaged with ostium 44.

Catheter 8 including stems 10 in accordance with the present invention offer considerable advantages. The catheter can be quickly and efficiently inserted while at the same time accurately positioning the tip or distal end of the stem in coaxial engagement with the ostium of the left coronary artery. Similarly, the catheter can be efficiently removed. The coaxial alignment of the tip within the ostium facilitates the insertion of interventional devices and minimiizes risk of trauma to the artery. Since the stem backs-up against (i.e., is engaged with) the contralateral wall of at least the ascending aorta (and preferably at least portions of the aortic arch) along a substantial portion of its length beginning at a location opposing the ostium, it provides a stable platform for deploying interventional devices and will support relatively high deployment forces. The relatively large-radius (i.e., gently curved) nature of the positioned catheter enables stents and other interventional devices to be deployed through the catheter with relatively low resistance. However, a small amount of resistance may occur as interventional devices reach the third arcuate section and tip of the catheter. Recognition of this resistance signal is a function of the cardiologist's deployment methods. This resistance-type feedback signal can be used as an indication that the interventional device is at the tip of the catheter. However, if substantial momentum is generated during deployment of the interventional device, the resistance signal may not be sensed. As a result of the above-described characteristics of the stem, relatively low amounts of trauma are imparted to the patient during catheterization procedures.

Although the preferred embodiment of the catheter has been described above as having contiguous arcuate and linear sections, relatively short intervening sections having different lengths and/or radii (not shown) could be included between the described sections while providing substantially the same characteristics and advantages described herein. By way of example, relatively short linear arcuate sections could be included between the above-described first, second, third and/or fourth sections while allowing a sufficient but not continuous length of the stem to back-up against the contralateral wall of the aorta to effectively function as the embodiments described herein.

The materials from which catheter 8, including stem 10, are fabricated, and other characteristics of the catheter such as the inner and outer diameters of the stem and body stock 12, can be similar or identical to known or otherwise conventional catheters. By way of example, the above-described shapes of stem 10 can be (without limitation) incorporated into Guidezilla® guide catheters available from Schneider (USA) Inc, of Minneapolis, Minn., the assignee of the present invention. Guide catheters of this type are disclosed, for example, in the Ju U.S. Pat. No. 5,403,292 and PCT Publication No. WO 95/15780. Other catheters which can include the shapes of stem 10 are disclosed in application Ser. Nos. 08/645,381 and 08/647,606, both of which were filed on May 13, 1996 and are assigned to the assignee of the present invention. The documents referred to above are hereby incorporated by reference in their entirety and for all purposes. Briefly, this embodiment of catheter 8 includes a body stock 12 and stem 10 (with the exception of tip 18) having a tri-layer construction which is illustrated generally in FIG. 5. As shown, the body stock 12 and sections 21–24 of stem 10 include an inner lining layer 61, intermediate reinforcement layer 62 and outer jacket layer 63. Catheters such as 8 typically have inner lumen diameters $D_1$ in the range between about 0.03 and 0.13 inches, and outer diameters $D_2$ in the range between about 0.05 and 0.15 inches (5 Fr–10 Fr). The embodiments of catheters 8 described above as Examples 1–7 have inner diameters $D_1$ between about 0.640 and 0.112 inches and outer diameters $D_2$ between about 0.78 and 0.130 inches.

As shown in FIG. 1, arcuate sections 21–23 and the portion of the fourth linear section 24 with the exception of tip 18 are constructed from two separate elements, stem transition tube section 66 and distal stem tube section 68. In one embodiment the inner lining layer 61 of stem transition tube section 66, which includes a portion of the arcuate section 22, is formed from a fluorocopolymer which is a compound of polyvinylidine fluoride (PVDF) and hexafluoropropylene (HFP). The reinforcement layer 62 of tube section 66 in this embodiment is formed by braided filaments such as 304 stainless steel. The outer jacket layer 63 of the tubular section 66 is a compound including 63.5% Polyamide, 36.0% $BaSO_4$, and 0.5% colorant.

Figure 5:
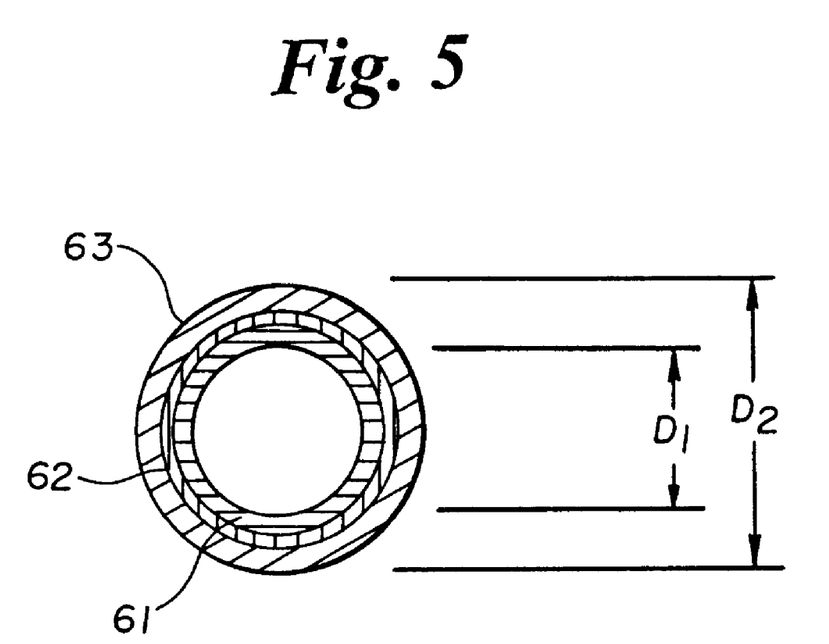
FIG. 5 is a cross sectional view of a tube from which the body stock and stem of the catheter shown in FIG. 1 can be formed.

Distal stem tube section 68 of stem 10 includes an inner lining 61 and reinforcement layer 62 which are identical to those of tube section 66 and described above. The outer jacket layer 63 of tube section 68 is a compound including 81.0% polyamide, 15.0% $BaSO_4$, and 4.0% $TiO_2$ as a colorant.

The tube section 70 of body stock 12 has an inner lining layer 61 and reinforcement layer 62 identical to those stem transition tube section 66 described above. Outer jacket layer 63 of tube section 70 is a compound including 63.5% polyamide, 36.0% $BaSO_4$ and 0.5% colorant.

Tip 18 is a tubular member formed from the same material at the outer jacket layer 63 of distal stem tubing section 68. The strain relief 16 can also be formed from the same material as the outer jacket layer 63 of the distal stem tubing section 68. Hub 14 can be formed from polycarbonate.

Tube section 70 of body stock 12, stem transition tube section 66 and distal stem tube section 68 are separately formed by extruding their inner lining layers 61. The braided stainless steel reinforcement layers 62 are then braided over layers 61. The outer jacket layers 63 are subsequently extruded over the reinforcement layers 62. Tube section 70 of body stock 12, stem transition tube section 66, distal stem tube section 68 and tip 18 are then bonded together by heat bonding or other known methods. At this point during the manufacture of catheter 8 the body stock 12 and stem 10 will typically be generally linear in form. The above-described shapes of stem 10 are imparted by positioning the assembled tubing sections onto a generally cylindrical but slightly flattened mandrel and subjecting them to relatively high temperatures. Stem 10 will then assume the curved shape of the mandrel.

Although the present mvention has been described with reference to preferred embodiments, those skilled in the art will recognize that changes can be made in form and detail without departing from the spirit and scope of the invention. Furthermore, all the documents identified herein are hereby incorporated by reference in their entirety and for all purposes.

What is claimed is:

1. A left coronary artery catheter comprising a flexible tubular member having a body stock and a stem with a distal end extending from a distal end of the body stock, the stem including:

a first section which is arcuate having a distal end, first free state radius and a first free state arc length disposed distally from the distal end of the body stock, at least a portion of the first section adapted to engage a continuous length of a contralateral wall of the ascending aorta when positioned within the patient with the stem distal end engaged with the ostium of the left coronary artery;

a second section which is arcuate having a distal end, a second free state radius and a second free state arc length disposed distally from the distal end of the first section toward the body stock;

a third section which is arcuate having a distal end, a third free state radius and a third free state arc length disposed distally from the distal end the second section away from the body stock;

the stem distal end adapted for engaging the ostium of a patient's left coronary artery; and wherein the first and second sections include arc lengths having a sum of at least about 210 degrees and distance lengths having a sum of at least about 2.5 inches, and the distal end of the stem extends toward the body stock or stem when the stem is in its free state.

2. The left coronary catheter of claim 1 and further including a fourth section which is linear having a distal end and a fourth length disposed distally from the distal end of the third section.

3. The left coronary catheter of claim 2 and further including a tip on the distal end of the fourth section, wherein the tip is softer than the fourth section.

4. The left coronary catheter of claim 2 wherein the first, second, third and fourth sections are contiguous with one another.

5. The left coronary catheter of claim 1 wherein the first section includes a first arc length less than about 200 degrees.

6. The left coronary catheter of claim 1 wherein the second section includes a second arc length less than about 150 degrees.

7. The left coronary catheter of claim 1 wherein the third section includes a third arc length less than about 60 degrees.

8. The left coronary catheter of claim 1 wherein the second and third sections include arc lengths having a sum between about 200 and 300 degrees.

9. The left coronary catheter of claim 1 wherein:
the first section includes a first arc length between about 125 and 180 degrees and a first radius between about 0.5 and 1.5 inches;
the second section includes a second arc length between about 85 and 140 degrees and a second radius between about 0.25 and 1.00 inches; and
the third section includes a third arc length between about 5 and 45 degrees and a third radius between about 0.25 and 0.75 inches.

10. The left coronary catheter of claim 7 and further including a fourth section which is linear having a distal end and a fourth length between about 0.10 and 0.75 inches disposed distally from the distal end of the third section.

11. The left coronary catheter of claim 10 and further including a tip on the distal end of the fourth section, wherein the tip is softer than the fourth section.

12. The left coronary catheter of claim 1 wherein:
the first section includes a first arc length between about 145 and 165 degrees and a first radius between about 0.75 and 1.25 inches;
the second section includes a second arc length between about 100 and 120 degrees and a second radius between about 0.40 and 0.80 inches; and
the third section includes a third arc length between about 5 and 35 degrees and a third radius between about 0.35 and 0.60 inches.

13. The left coronary catheter of claim 12 and further including a fourth section which is linear having a fourth length between about 0.10 and 0.25 inches disposed distally from the distal end of the third section.

14. The left coronary catheter of claim 13 and further including a tip on the distal end of the fourth section, wherein the tip is softer than the fourth section.

15. The left coronary catheter of claim 1 wherein:
the first section includes a first arc length of about 155 degrees and a first radius between about 0.85 and 1.00 inches;
the second section includes a second arc length of about 110 degrees and a second radius between about 0.40 and 0.75 inches; and
the third section includes a third arc length between about 10 and 30 degrees and a third radius between about 0.40 and 0.55 inches.

16. The left coronary catheter of claim 15 and further including a fourth section which is linear having a distal end and a fourth length of about 0.15 inches disposed distally from the distal end of the third section.

17. The left coronary catheter of claim 14 and further including a tip on the distal end of the fourth section, wherein the tip is softer than the fourth section.

18. The left coronary catheter of claim 1 wherein the first, second and third sections are contiguous with one another.

19. A left coronary catheter configured to be directed to an ostium of a patient's left coronary artery through a descending aorta, aortic arch and ascending aorta, comprising a flexible tubular body stock having a distal end and a non-linear stem extending from the distal end of the body stock, the stem including a distal end adapted for engaging the ostium of a patient's left coronary artery, a first section which is arcuate having a distal end, a first free state radius and a first free state arc length between the distal end of the stem and the body stock, a second section which is arcuate having a distal end, a second free state radius and a second free state arc length between the first section and the distal end of the stem, and a third section which is arcuate having a distal end, third free state radius and a third free state arc length between the second section and the distal end of the stem, wherein the first and second sections extend toward the body stock in their free state, the third section extends away from the body stock in its free state, the first and second sections include arc lengths having a sum of at least about 210 degrees and distance lengths having a sum of at least about 2.5 inches, the distal end of the stem extends toward the stem or body stock when the stem is in its free state, and the arc lengths and radii of the first, second and third sections are adapted to cause at least a portion of the stem to engage a continuous length of a contralateral wall of the ascending aorta from a location opposing the ostium of the left coronary artery when positioned within the patient with the distal end engaged with the ostium of the left coronary artery.

20. The left coronary catheter of claim 19 wherein the second free state radius is less than the first free state radius.

21. The left coronary catheter of claim 20 wherein the second free state arc length is less than the first free state arc length.

22. The left coronary catheter of claim 19 wherein the second free state arc length is less than the first free state arc length.

23. The left coronary catheter of claim 19 wherein the first section of the stem is contiguous with the body stock.

24. The left coronary catheter of claim 23 wherein the second section of the stem is contiguous with the first section of the stem.

25. The left coronary catheter of claim 24 wherein the third section of the stem is contiguous with the second section of the stem.

26. The left coronary catheter of claim 25 wherein the stem further includes a fourth section having a fourth length extending from and contiguous with the third section of the stem.

27. The left coronary catheter of claim 19 wherein the second section of the stem is contiguous with the third section of the stem.

28. The left coronary catheter of claim 27 wherein the stem further includes a fourth section having a fourth length extending from and contiguous with the third section of the stem.

29. The left coronary catheter of claim 19 wherein:
the first section includes a first arc length between about 125 and 180 degrees and a first radius between about 0.5 and 1.5 inches;
the second section includes a second arc length between about 85 and 140 degrees and a second radius between about 0.25 and 1.00 inches; and
the third section includes a third arc length between about 5 and 45 degrees and a third radius between about 0.25 and 0.75 inches.

30. The left coronary catheter of claim 29 and further including a fourth section which is linear having a fourth length between about 0.10 and 0.75 inches disposed distally from the distal end of the third section.

31. The left coronary catheter of claim 19 wherein:
the first section includes a first arc length between about 145 and 165 degrees and a first radius between about 0.75 and 1.25 inches;
the second section includes a second arc length between about 100 and 120 degrees and a second radius between about 0.40 and 0.80 inches; and
the third section includes a third arc length between about 5 and 35 degrees and a third radius between about 0.35 and 0.60 inches.

32. The left coronary catheter of claim 31 and further including a fourth section which is linear having a fourth length between about 0.10 and 0.25 inches distally disposed from the distal end of the third section.

33. A left coronary catheter configured to be directed to an ostium of a patient's left coronary artery through a descending aorta, aortic arch and ascending aorta, the catheter comprising a flexible tubular body stock having a distal end, and a curved stem extending from the distal end of the body stock, the stem including an engagement portion and a distal end adapted for engaging the ostium of a patient's left coronary artery, the stem sized and configured such that the distal end of the stem extends toward a portion of one of the body stock and stem when the stem is in its free state and the engagement portion engages a continuous length of a contralateral wall of the ascending aorta from a location opposing the ostium of the left coronary artery when positioned within the patient with the stem distal end engaged with the ostium of the left coronary artery.

34. The left coronary catheter of claim 14 wherein the curved stem includes first and second curved parts and the engagement portion comprises at least part of the first curved part and the stem distal end is the distal-most end of a second curved part.

35. The left coronary catheter of claim 34 wherein the first curved part comprises an arcuate first section having a distal end, a first free state radius and a first free state arc length disposed distally from the distal end of the body stock, and the second curved part comprises an arcuate second section having a distal end, a second free state radius and a second free state arc length disposed distally from a distal end of the first section and exiting away from the body stock.

36. The left coronary catheter of claim 35 wherein the first curved part further comprises a third arcuate section having a third free state radius and a third free state arc length disposed intermediate the first and second arcuate sections and extending toward the body stock.

37. The left coronary catheter of claim 36 wherein the second curved part further comprises a linear fourth section having a distal end and a fourth length disposed distally from a distal end of the second section.

38. The left coronary catheter of claim 37, further comprising a tip on a distal end of the fourth section, wherein the tip is softer than the fourth section.

39. The left coronary catheter of claim 34 wherein the first curved part extends through a radical angle between about 220 and 305 degrees and has at least one radius of curvature between 0.4 and 1.5 inches.

40. The left coronary catheter of claim 39 wherein the second curved part extends through a radial angle between about 5 and 35 degrees and has at least one radius of curvature between about 0.35 and 0.60 inches.

41. The left coronary catheter of claim 33 wherein the curved stem has an arc length of at least about 210 degrees and a distance length of at least about 2.5 inches.

* * * * *

UNITED STATES PATENT AND TRADEMARK OFFICE
CERTIFICATE OF CORRECTION

PATENT NO. : 5,971,974
DATED : October 26, 1999
INVENTOR(S) : Kiesz et al.

It is certified that error appears in the above-identified patent and that said Letters Patent is hereby corrected as shown below:

ON THE TITLE PAGE:

Item [75] delete "Keisz" and insert therefor --Kiesz--

Column 9, line 25, delete "7" and insert therefor --9--

Column 9, line 63, delete "14" and insert therefor --16--

Column 11, line 32, delete "14" and insert therefor --33--

Column 12, line 2, delete "a" and insert therefor --the--

Column 12, line 10, delete "exiting" and insert therefor --extending--

Column 12, line 24, delete "radical" and insert therefor --radial--

Signed and Sealed this

Twenty-third Day of January, 2001

Attest:

Attesting Officer

Q. TODD DICKINSON
Commissioner of Patents and Trademarks

US005971974C1

(12) EX PARTE REEXAMINATION CERTIFICATE (5132nd)
United States Patent
Kiesz (10) Number: US 5,971,974 C1
(45) Certificate Issued: Jul. 5, 2005

(54) LEFT CORONARY ARTERY CATHETER (75) Inventor: Radoslaw Stefan Kiesz, San Antonio, TX (US)

(73) Assignee: Schneider (USA) Inc., Plymouth, MN (US)

Reexamination Request:
No. 90/005,781, Jul. 31, 2000

Reexamination Certificate for:
Patent No.: 5,971,974
Issued: Oct. 26, 1999
Appl. No.: 08/707,458
Filed: Sep. 3, 1996

Certificate of Correction issued Jan. 23, 2001.

Related U.S. Application Data

(60) Provisional application No. 60/003,309, filed on Sep. 6, 1995.

(51) Int. Cl.[7] .............................................. A61M 25/00
(52) U.S. Cl. ...................................... 604/523; 604/264
(58) Field of Search ................................. 604/507, 508, 604/93.01, 171, 264, 523, 524, 525, 528, 532

(56) References Cited

U.S. PATENT DOCUMENTS 5,445,625 A   8/1995   Voda .......................... 604/281

*Primary Examiner*—Sharon Kennedy (57) ABSTRACT

A left coronary catheter including a hub, a linear flexible tubular body stock extending from the hub and a curved flexible tubular stem extending from the body stock. The curved stem includes a first, arcuate section extending from a distal end of the body stock, a second, arcuate section from a distal end of the first section, a third, arcuate section extending from a distal end of the second section, and a fourth, linear section including a soft tip extending from a distal end of the third section. The first and second sections curve toward the body stock. The third section curves away from the body stock.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–32 is confirmed.

Claim 33 is determined to be patentable as amended.

Claims 34–41, dependent on an amended claim, are determined to be patentable.

33. A left coronary catheter configured to be directed to an ostium of a patient's left coronary artery through a descending aorta, aortic arch and ascending aorta, the catheter comprising a flexible tubular body stock having a distal end, and a curved stem extending from the distal end of the body stock, the stem including an engagement portion and a distal end adapted for engaging the ostium of a patient's left coronary artery, the stem sized and configured such that the distal end of the stem extends toward a portion of one of the body stock and stem when the stem is in its free state and the engagement portion engages a continuous length of a contralateral wall of the [ascending aorta from] *aorta beginning at* a location opposing the ostium of the left coronary artery *and extending along the wall of the ascending aorta and aortic arch to at least the left subclavian artery* when positioned within the patient with the stem distal end engaged with the ostium of the left coronary artery.

* * * * *